United States Patent [19]

Takeuchi et al.

[11] Patent Number: 4,736,311

[45] Date of Patent: Apr. 5, 1988

[54] PARTICLE SIZE DISTRIBUTION MEASURING APPARATUS

[75] Inventors: Kanau Takeuchi, Kyoto; Kazuhiro Hayashida, Joyo; Shozo Yano, Uji, all of Japan

[73] Assignee: Shimadzu Corporation, Kyoto, Japan

[21] Appl. No.: 715,007

[22] Filed: Mar. 22, 1985

[30] Foreign Application Priority Data

Apr. 25, 1984 [JP] Japan .................................. 59-84906

[51] Int. Cl.$^4$ ..................... G01N 23/02; G01N 15/04; G06F 15/42
[52] U.S. Cl. .................... 364/555; 73/865.5; 356/335
[58] Field of Search ............ 364/555; 378/51; 356/335, 336; 73/432 PS; 324/71.4; 377/12; 494/10

[56] References Cited

U.S. PATENT DOCUMENTS

| | | | |
|---|---|---|---|
| 4,318,180 | 3/1982 | Lundquist et al. | 364/555 |
| 4,478,073 | 10/1984 | Holsworth et al. | 73/432 PS |
| 4,488,248 | 12/1984 | Okada et al. | 364/555 |

OTHER PUBLICATIONS

Shozo Yano et al., "The Particle Size Analyzer with Built-In Microcomputer", Shimadzu Review, vol. 38, No. 3 (1981), pp.207-215.

*Primary Examiner*—Felix D. Gruber
*Attorney, Agent, or Firm*—Koda and Androlia

[57] ABSTRACT

An apparatus for measuring the size distribution of particles by making use of centrifugal force field, comprising a mechanism for making a suspension revolve, an optical unit for detecting a light absorption by the suspension, and a micro-computer. The suspension suspends test particles whose size distribution is to be measured. The optical unit measures a time-dependent particle concentration variation due to the particle movements forced in a centrifugal force field produced by the revolution of the suspension. The micro-computer is provided with a memory for storing equations to obtain the size distribution of particles from the measured particle concentration variation and equations for correcting adverse effects by non-parallel particle movements in a centrifugal force field, to give a particle size distribution free from the error arising from the non-parallel movements of particles.

3 Claims, 3 Drawing Sheets

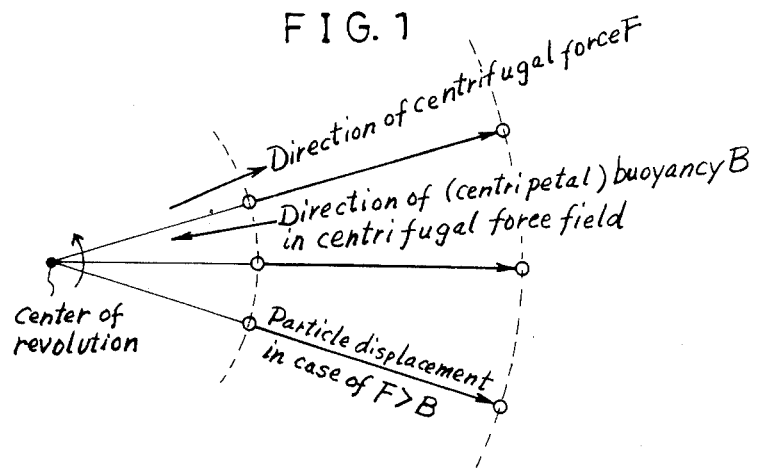
FIG. 1
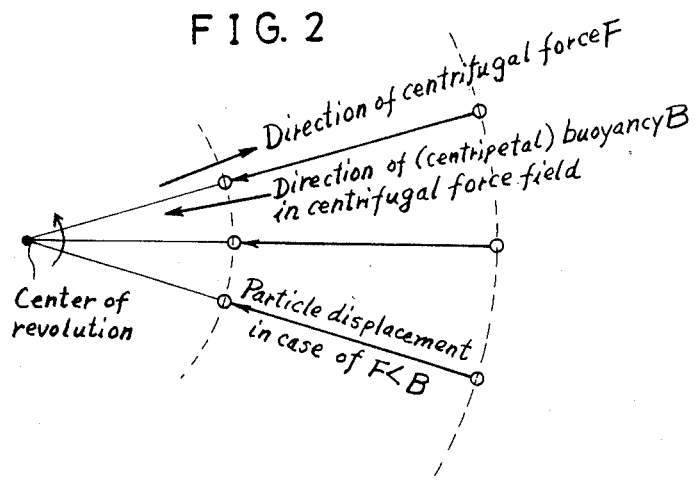
FIG. 2
FIG. 4
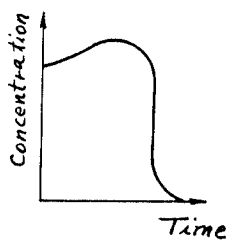
Centripetal Movement
FIG. 3
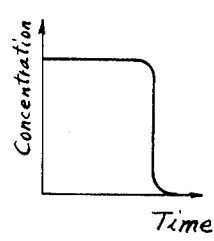
Vertical Movement
FIG. 5
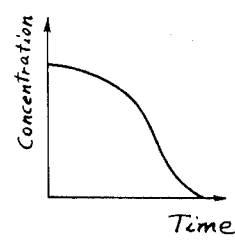
Centrifugal Movement

PARTICLE SIZE DISTRIBUTION MEASURING APPARATUS

BACKGROUND OF THE INVENTION

1. Field of the Invention

The present invention relates to a particle size distribution measuring apparatus, and more particularly to an apparatus for measuring the size distribution of particles by making use of a centrifugal force field.

2. Prior Art

If a suspension is made to revolve, it is put in a centrifugal force field produced by the revolution of the suspension. Therefore, all the solid particles suspended in the suspension receive their respective forces, and begin to move in the suspension. The movements of these particles can be used for measuring the size distribution of the particles. In this case, the resultant force acting on each of the particles is the sum of a centrifugal force and a "buoyancy", because the particles are "immersed" in a liquid medium which, together with the particles, constitutes the suspension. The buoyancy in a centrifugal force field is "centripetal" and depends not only on the density of the medium but also on the position in the suspension, being different from an ordinary buoyancy in the gravitational field. A conventional apparatus for measuring the size distribution of particles by making use of a centrifugal force field commonly comprises a sample vessel, a mechanism for making the sample vessel revolve at a high speed and a particle concentration detector. The sample vessel is to hold a suspension containing test particles whose size distribution is to be measured. The suspension is prepared by making a suitable liquid medium suspend the test particles. With the sample vessel containing the test particles made to revolve at a high speed, the particles begin to move in the suspension owing to the centrifugal force field produced by the revolution. The movements of the particles cause the local particle concentrations (which were uniform throughout the suspension initially) to vary with the passage of time. The moving speeds of the particles are determined from the centrifugal forces and the centripetal buoyancies, both acting on the particles, and from the viscosity of the medium. In addition the centrifugal forces and the buoyancies depend on the sizes and positions of the particles. Therefore, the time-dependent variation of the particle concentration at a position in the suspension gives information about the size distribution of the particles. The particle concentration is detected by said particle concentration detector in the apparatus.

In such a method of measuring the size distribution of particles, it should be noticed that the observed particle concentration is influenced also by a factor not related to the particle sizes. Whether the resultant forces acting on the particles are centrifugal or centripetal, the movements of the particles in a centrifugal force field are not parallel to one another but radial. Therefore, the particle concentration and its time-dependent variation to be observed depend also on the position of concentration detection. The inventors of the present invention have already proposed, in Japanese Patent Application No. 56-214707, a measure to correct the error arising the measured particle size concentration owing to non-parallel centrifugal movements of the particles. However, correction is also necessary to correct for non-parallel centrifugal movements expected when the density of the particles is smaller than that of the liquid medium of the suspension.

By the way, a buoyancy acting on a particle in a suspension put in a centrifugal force field is proportional to the centrifugal force acting on the particle, but it is directed opposite to the centrifugal force. In other words, the buoyancy in a centrifugal force field is centripetal. Therefore, if the centrifugal forces acting on the suspended particles are larger than the buoyancies acting on the same, the resultant forces are still centrifugal, so the movements of the particles are directed outward from the center of revolution of the suspension. On the contrary, if the buoyancies overwhelm the centrifugal forces, the particles receive centripetal forces and move toward the center of revolution of the suspension. As is understood from the previous description about the error arising from the non-parallel movements of the particles, the centrifugal movements of the particles cause the seeming particle concentration to be observed smaller, while the centripetal movements cause the particle concentration to be observed larger. Such being the case, the measure to correct the error due to the non-parallel movements of particles is necessarily designed so as to be applicable to both the two directions of the particle movements.

OBJECTS AND SUMMARY OF THE INVENTION

An object of the present invention is to provide an apparatus for measuring the size distribution of particles by making use of a centrifugal force field, which apparatus is made free from the non-parallel centrifugal or centripetal particle movements in the centrifugal force field.

Another object of the present invention is to make such an apparatus desired so as to be capable also of making use of gravitation in measuring the size distribution of particles.

The principle of the present invention is as follows.

The moving speed V of a particle in a suspension put in a centrifugal force field produced by the revolution of the suspension is determined from a centrifugal force and a centripetal force, both acting on the particle, and Stokes' law. As a result the moving speed V of the particle is given by:

$$V = \frac{R\omega^2(\rho_1 - \rho_p)D_p^2}{18\eta}, \tag{1}$$

where R is the position of the particle measured from the center of revolution of the suspension, $\omega$ the angular velocity of the revolution, $\rho_1$ the density of the liquid medium of the suspension, $\rho_p$ the density of the particle, $D_p$ the diameter of the particle, and $\eta$ the viscosity of the liquid medium. In this equation, a positive (+) value of V (obtained in case the density $\rho_1$ of the medium is larger than the density $\rho_p$ of the particle) means a centripetal movement, while a negative (−) value of V (obtained in case of $\rho_1 < \rho_p$) means a centrifugal movement.

With a suspension made to revolve, all the suspended particles having various diameters move at their respective speeds given by Eq. (1), and accordingly the local particle concentrations in the suspension vary with lapse of time after the initiation of the suspension revolution. The time-dependent variations of the particle concentration at a certain position in the suspension are observed by a particle concentration detector. On the other hand, the time t needed for the particle with a diameter of $D_p$ to reach the particle concentration detecting position from either end portion of the suspension is obtained by integrating the inverse of Eq. (1) with respect to R. The integration $\int(1/v)dR$ gives:

$$t = \frac{1.05\eta}{N^2(\rho_1 - \rho_p)D_p^2} \cdot \log\frac{R_1}{R_2}, \quad (2)$$

and $$t = \frac{1.05\eta}{N^2(\rho_p - \rho_1)D_p^2} \cdot \log\frac{R_2}{R_3}, \quad (3)$$

for a centripetal movement and a centrifugal movement, respectively. In the equations $N(=\omega/2\pi)$ is the number of revolutions per second, and $R_1$, $R_2$ and $R_3$ are the distance of the outside end of the suspension, the distance of the position where the particle concentration is observed, and the distance of the inside end of the suspension, all being measured from the center of revolution of the suspension. Eqs. (2) and (3) show that the time needed for the particles to reach the particle concentration detecting position $R_2$ is shorter with an increase in particle diameters. Therefore, if the particle concentration is observed to be a certain value at a time t, the time t is also the instance at which all the particles whose diameters are larger than a diameter related to that time t by Eq. (2) (or Eq. (3)) finished passing the particle concentration detecting position $R_2$. The size distribution of the particles can be derived from the relationships among the observed particle concentration, the time t when the particle concentration was detected, and the diameter related to that time t by Eq. (2) (or Eq. (3)).

However, the above description of measuring the size distribution of particles ignores the previously mentioned effect by the non-parallel movements of the particles on the observed particle concentration. In case the resultant forces acting on the particles are centripetal, that is, the centrifugal forces acting on the particles due to the revolution of the suspension are overwhelmed by the (centripetal) buoyancies in the centrifugal force field because of $\rho_1 < \rho_p$, the particles move in the directions converging toward the center of revolution of the suspension, having their tangential spacings made narrower and narrower, as illustrated by FIG. 2. This causes the particle concentration to be larger. On the contrary, in case the resultant forces acting on the particles are centrifugal, that is, the centrifugal forces are larger than the (centripetal) buoyancies (because of $\rho_1 < \rho_p$), the particles move in the directions diverging outward from the center of revolution of the suspension, broadening their tangential spacing, as illustrated in FIG. 1. Therefore, the particle concentration is made smaller.

To make the effects of these non-parallel movements of particles understood more easily, first consider a suspension in which all the suspended particles have the same diameter, and further suppose that the suspension be left in the gravitational field. All the particles in the suspension, receiving the same (downward) gravitational force and the same (upward) ordinary buoyancy, move downward (in case the gravity is larger than the buoyancy) or upward (in case the gravity is overwhelmed by the buoyancy) in parallel with one another. In this case the particle concentration is observed to be constant, as is qualitatively illustrated by FIG. 3, until it abruptly decreases to zero when all the particles finish passing the concentration detecting position. In contrast with this, if this suspension is placed in a centrifugal force field, the resultant forces acting on the particles are centripetal or centrifugal, as is mentioned above. Receiving the centripetal forces the particles move in converging directions, so the particle concentration is observed to increase temporarily, as is shown qualitatively in FIG. 4, before it decreases to zero with all the particles passing the concentration detecting position. On the other hand, in case of the resultant forces being centrifugal the particle movements diverge radially (FIG. 2), and accordingly the particle concentration is observed, as is shown qualitatively in FIG. 5, to decrease monotonously to zero owing to both the diverging particle movements and the passage of all the particles through the concentration detecting position. Such tendencies of the time-dependent particle concentration variations are seen also in the case in which the suspended particles have their diameters not kept equal, but distributed widely. In any case the observed time-dependent variations of the particles in a centrifugal force field depend not only on the passage of the particles through the concentration detecting position but also on the variations of the tangential inter-particle spacings caused by the non-parallel movements of the particles.

The effects by the non-parallel particle movements on the particle concentration variations can be corrected with two groups of equations shown in the following as Eqs. (4) and Eqs. (5), which give oversize concentrations $C_i$ for the centripetal particle movements and for the centrifugal particle movements, respectively. In those equations, $C_0$ ($=1$) is the oversize concentration for the particles having an infinitesimally small diameter ($D_p=0$); $C_1, C_2, \ldots, C_{2n}$ are the oversize concentrations for various-sized particles; $\gamma_1, \gamma_2, \ldots, \gamma_{2n}$ are the parameters related to observed concentrations; suffices $1, 2, \ldots, 2n$ are numerals indicating the divisions of particle sizes, smaller numerals representing the divisions corresponding to smaller particle sizes; K is a constant determined from both the distance of the outside end of the suspension and the distance of the concentration detecting position, both being measured from the center of revolution of the suspension; and K' is a constant determined from both the distance of the inside end of the suspension and the distance of the concentration detecting position, both being measured from the center of revolution of the suspension.

$$C_1 = C_0 + \frac{2K}{(1-2K)e^{2K}-1} \cdot \gamma_1.$$

$$C_2 = \frac{e^{-2K}}{1-\frac{K}{3}}\left\{\left(1+\frac{K}{3}\right)C_0 + \frac{4}{3}Ke^K C_1 - \gamma_2\right\}.$$

$$\vdots$$

$$C_{2n-1} = \frac{e^{-2K}}{1-\frac{2K}{3(2n-1)}}\left[\left\{\left(\frac{2n-1}{K} - \frac{(2n-1)^2}{2K^2}\right)e^{\frac{2K}{2n-1}} + \frac{2n-1}{2C^2}\right\}C_0 + \right.$$

$$\left\{-\frac{(2n-1)^2}{2K^2} + \left(1 - \frac{2n-1}{K} + \frac{(2n-1)^2}{2K^2} + \frac{2K}{3(2n-1)}\right)e^{\frac{2K}{2n-1}}\right\}C_1 +$$

$$\frac{8K}{3(2n-1)}e^{\frac{4K}{2n-1}}C_2 + \frac{4K}{3(2n-1)}e^{\frac{6K}{2n-1}}C_3 + \ldots + \frac{8K}{3(2n-1)}e^{\frac{2nK}{2n-1}}C_{2n} - \gamma_{2n-1}\cdots.$$

$$C_{2n} = \frac{e^{-2K}}{1-\frac{K}{3n}}\left\{\left(1+\frac{K}{3n}\right)C_0 + \frac{4K}{3n}e^{\frac{K}{n}}C_1 + \frac{2K}{4n}e^{\frac{2K}{n}}C_2 + \ldots + \frac{4K}{3n}e^{\frac{2n-1}{n}K}C_{2n-1} - \gamma_{2n}\right\}.$$

$$\Bigg\}(4)$$

$$C_1 = C_0 - \frac{2K'^2}{1-(1+2K')e^{-2K'}} \cdot \gamma_1.$$

$$C_2 = \frac{e^{2K'}}{1+\frac{K'}{3}}\left\{\left(1-\frac{K'}{3}\right)C_0 + \frac{4}{3}K'e^{-K'}C_1 - \gamma_2\right\}.$$

$$\vdots$$

$$C_{2n-1} = \frac{e^{2K'}}{1+\frac{2K'}{3(2n-1)}}\left[\left\{\left(\frac{(2n-1)^2}{2K'^2} - \left(\frac{2n-1}{K'} + \frac{(2n-1)^2}{2K'^2}\right)e^{-\frac{2K'}{2n-1}}\right)C_0 + \right.\right.$$

$$\left\{-\frac{(2n-1)^2}{2K'^2} + \left(1 + \frac{2n-1}{K'} + \frac{(2n-1)^2}{2K'^2} - \frac{2K'}{3(2n-1)}\right)e^{-\frac{2K'}{2n-1}}\right\}C_1 -$$

$$\frac{8K'}{3(2n-1)}e^{-\frac{4nK'}{2n-1}}C_2 - \frac{4K'}{3(2n-1)}e^{-\frac{6K'}{2n-1}}C_3 - \ldots - \frac{8K'}{3(2n-1)}e^{-\frac{4nK'}{2n-1}}C_{2n-2} - \gamma_{2n-1}\right].$$

$$C_{2n} = \frac{e^{2K'}}{1+\frac{K'}{3}}\left\{\left(1-\frac{K'}{3n}\right)C_0 - \frac{4K'}{3n}e^{-\frac{K'}{n}}C_1 - \frac{2K'}{3n}e^{-\frac{2K'}{n}}C_2 - \ldots - \frac{4K'}{3n}e^{-\frac{2n-1}{n}K'}C_{2n-1} - \gamma_{2n}\right\}.$$

$$\Bigg\}(5)$$

The apparatus according to the present invention is provided with a memory for storing two particle concentration correcting programs based on Eqs. (4) and Eqs. (5), respectively, and is designed to be capable of correcting observed particle concentrations with respect to both the centripetal and the centrifugal movements of particles with one of the two programs selected.

BRIEF DESCRIPTION OF THE DRAWINGS

The present invention will be described further in detail with reference to the attached drawings, in which:

FIGS. 1 and 2 are drawings illustrating the movements of particles in a suspension put in a centrifugal force field;

FIG. 3 shows a qualitative concentration variation of particles in a suspension put in a gravitational field;

FIGS. 4 and 5 show qualitative concentration variations of particles in a suspension put in a centrifugal force field;

DETAILED DESCRIPTION OF THE INVENTION

Figure 6:
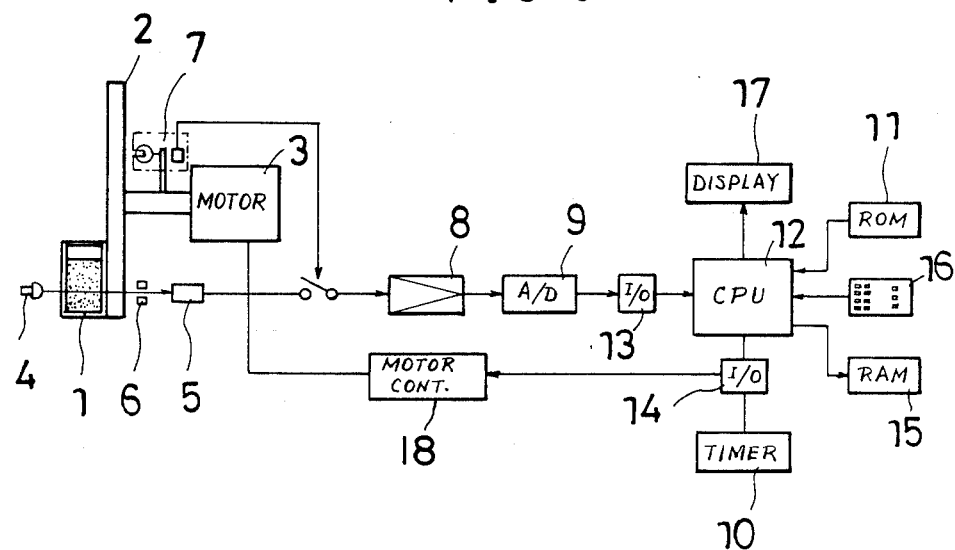
FIG. 6 shows the constitution of an embodiment of the present invention.

In the first place, the constitution of an embodiment of the invention is described according to FIG. 6. A sample vessel 1 mounted on a turning disc 2 is to contain a suspension in which are suspended sample particles whose size distribution is to be measured. The turning disc 2, which is rotated by a motor 3, makes the sample vessel 1 revolve to put the suspension in a centrifugal force field. A light source 4, a slit 6 and a light detector 5 constitute a unit for detecting the light absorption related to the particles concentration at a predetermined position in the suspension. The particle concentration is given by an intensity of the light transmitted to the light detector 5 through the suspension. A position detector 7 is to make the output from the light detector 5 taken out only when the revolving sample vessel 1 (therefore, the suspension) comes to the position where said predetermined position in the suspension can be irradiated by the light source 4. The output from the light detector 5 is amplified by an amplifier 8, converted to a digital signal by an A-D converter 9, and then inputted to a CPU 12 through an input-output interface 13. The CPU 12 has further connections with a timer 10 (through an input-output interface 14), a RAM 15, a keyboard 16, a ROM 11 and a display unit 17. The timer 10 measures the time laps since the application of centrifugal force to the suspension. The RAM 15 has areas for memorizing various measurement conditions and computed results. The keyboard 16 is for setting the measurement conditions and for starting a measurement. The ROM 11 stores the above Eqs. (2) and (3) relating a particle diameter $D_p$ to the time t needed for the particle having the diameter $D_p$ to reach the particle concentration detecting position in the suspension, Eqs. (4) and Eqs. (5) for correcting the effects of the non-parallel particle movements, and a program for measuring the size distribution in the gravitational force field, in which program the correction by Eqs. (4) and (5) is not carried out. The rotation of the motor 3 is controlled by a motor drive controller 18. A series of optical signals related to the particle concentration variation at a position in the suspension are continually inputted to the CPU 12 from the light detector 5 through the amplifier 8, A-D converter 9 and interface 13, and dealt with by the CPU 12 so as to give the size distribution of the particles in the suspension. The obtained size distribution of the particles is displayed on the display unit 17. Further, the present invention is devised so as also to be capable of using the gravitational field instead of centrifugal force field. In this case, measurement is of course carried out with the sample vessel 1 kept standing still. The program to be used for the measurement by means of the gravitational field is also stored in the ROM 11.

Figure 7:
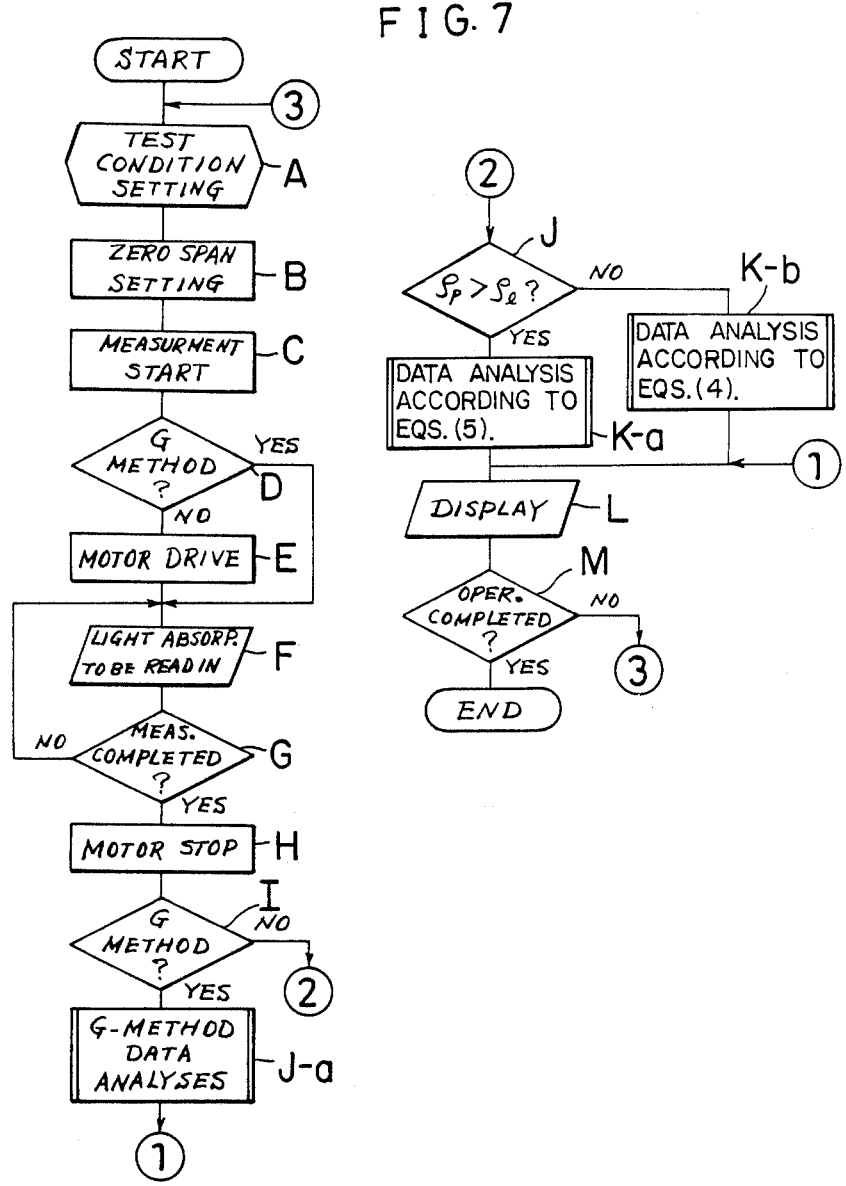
FIG. 7 shows a flow-chart of the program for measuring the size distribution of particles by the above embodiment.

The process of measuring the size distribution of particles by this embodiment is described in the following with reference to FIG. 7, which shows a flow chart representing the program stored in the ROM 11.

In advance of measurement, the measurement conditions are set (step A) by inputting the data such as the mass density $\rho_p$ of the particles to have their size distribution measured, the density $\rho_1$ of the liquid medium which, together with the particles, constitutes a suspension, the viscosity $\eta$ of the medium, the number of revolutions N (per unit time) of the suspension, the distances $R_i$ (i=1, 2, 3) appearing in Eqs. (2) and (3), and then a zero span is also set (step B). After the above preparations, the suspension is charged in the sample vessel 1, and then measurement is commenced (step C).

In case the measurement by means of the gravitational field is instructed by an operation of the keyboard 16, step D is followed by step F with step E jumped over, and the light absorption by the suspension is continuously detected by the light detector 5, with the motor 3 kept non-rotated. The detected light absorption continues to be read in (step F) by the RAM 15, until the detected absorption is judged (step G) to have decreased to a predetermined value. When the light absorption reaches the predetermined value, the CPU 12, using the data in the RAM 15, computes (step J-a) the size distribution of the particles in the suspension according the data treatment method in case of using the gravitational field. The obtained size distribution is displayed on the display unit 17 (step L).

In case of the measurement by means of a centrifugal force field, step D is followed by step E and the motor 3 starts rotating (step E) to make the suspension revolve. The RAM 15 continues to read in (step F) the data outputted continually from the light detector 5 about the light absorption by the suspension. When the light absorption reaches a predetermined value (step G), the motor 3 is stopped at step H, which is followed by step J through step I. At step J the magnitudes of $\rho_p$ and $\rho_1$ are compared with each other, both the data having been inputted to the apparatus in the beginning. If $\rho_p$ is smaller than $\rho_1$, the particle movements are judged to be centripetal. In this case, step J is followed by step K-b where the time t at which the light absorption was detected is converted to the particle diameter $D_p$ with Eq. (2), and the size distribution corrected with respect to the converging particle movements is obtained with Eqs. (4). The particle size distribution thus obtained is displayed on the display unit 17 (step L). On the other hand, if $\rho_p$ is larger than $\rho_1$, the particle movements are judged to be centrifugal at step J, and the size distribution is computed with Eq. (3) and Eqs. (5) at step K-a.

In the above embodiment, the magnitudes of $\rho_p$ and $\rho_1$ are automatically compared by the apparatus. However, it is possible also to devise the apparatus so that the comparison by an operator may be manually inputted to the apparatus. Further, Eqs. (4) and Eqs. (5) stored in the ROM 11 can be replaced with the correction parameters computed with these equations in advance under certain conditions. Instead of the visible light used to detect the particle concentration in the suspension, other forms of radiation may be used, such as X-rays.

As is easily understood from the above descriptions, the present invention makes it possible to correct the effect of non-parallel movements of the particles in a suspension in a centrifugal force field both in case the resultant forces acting on the particles are centripetal and in case they are centrifugal, so that the size distribution of the particles can be measured without an error due to a seeming particle concentration affected by non-parallel particle movements.

What is claimed is:

1. A particle size distribution measuring apparatus based upon the principle that particles suspended in a suspension put under a centrifugal force field move at their respective different speeds determined by their respective sizes along force lines in the centrifugal force field, said apparatus comprising:

a revolving mechanism for revolving a suspension for the purpose of putting the same under a centrifugal force field, said suspension containing therein particles whose size distribution is to be measured;

a concentration detecting means for detecting the time-dependently varying particle concentration at a predetermined position in said suspension;

a memory for storing a sequence program for deriving the particle size distribution of said particles from the data outputted from said concentration detection means, said sequence program including:
   (1) a first correction program for correcting with oversize concentrations $C_i$ ($i=1, 2, 3 \ldots$) a first error arising in the particle size distribution obtained only from the data from said concentration detecting means owing to non-parallel centripetal movements of said particles in said centrifugal force fields said centripetal movements appearing when the density of said particles is smaller than that of the medium liquid of said suspension, said oversize concentrations $C_1$ being given by $$C_1 = C_0 + \frac{2K}{(1-2K)e^{2K}-1} \cdot \gamma_1, \text{ and}$$

$$C_{2n} = \frac{e^{-2K}}{1-\frac{K}{3n}}\left(\left(1+\frac{K}{3n}\right)C_0 + \frac{4K}{3n}e^{\frac{K}{n}}C_1 + \frac{2K}{4n}e^{\frac{2K}{n}}C_2 + \ldots + \frac{4K}{3n}e^{\frac{2n-1}{n}K}C_{2n-1} - \gamma_{2n}\right)$$

($C_0=1$; n: half integers excluding $\frac{1}{2}$) where $K=\ln(R_1/R_2)$, $R_1$ being the bottom position of said suspension and $R_2$ being the bottom position of said suspension, both being measured from the center revolution of said revolving mechanism, and $\gamma_i$ are the particle concentrations detected by said concentration detecting means; and (2) a second correction program for correcting with oversize concentration $C'_i$ ($i=1, 2, 3 \ldots$) a second error arising correspondingly to said first error owing to non-parallel centrifugal movements of said particles in said centrifugal force field, said centrifugal movements appearing when the density of said particle is larger than that of the medium liquid of said suspension, said oversize concentrations $C'_1$ being given by $$C'_1 = C_0 - \frac{2K'^2}{1-(1+2K')e^{-2K'}} \cdot \gamma_1, \text{ and}$$

$$C'_{2n} = \frac{e^{2K'}}{1+\frac{K'}{3}}\left(\left(1-\frac{K'}{3n}\right)C_0 - \frac{4K'}{3n}e^{-\frac{K'}{n}}C_1 - \frac{2K'}{3n}e^{-\frac{2K'}{n}}C_2 - \ldots - \frac{4K'}{3n}e^{-\frac{2n-1}{n}K'}C_{2n-1} - \gamma_{2n}\right),$$

($C'_0=1$; n: half integers excluding $\frac{1}{2}$) where $K'=\ln(R_1/R_3)$, $R_1$ being the position of concentration detection and $R_3$ being the liquid-surface position of said suspension, both being measured from the center of revolution of said suspension, and $\gamma_i$ are the particle concentrations detected by said concentration detecting means;

a CPU for computing a particle size distribution of said particles according to the data from said concentration detecting means and to said first correction program or said second correction program; and an input means for inputting, in advance, the information on the relative magnitude between the density of said particles and that of the medium liquid of said suspension with a view to making said CPU select either said first correction program when the density of said particle is smaller than that of the medium liquid of said suspension or said second correction program when the density of said particles is larger than that of the medium liquid of said suspension.

2. A particle size distribution measuring apparatus as defined in claim 1, wherein said concentration detecting means comprises a light source and a photosensor, both being arranged so that a light path between them may cross said suspension at a predetermined position once a revolution.

3. A particle size distribution measuring apparatus as defined in claim 1, wherein said concentration detecting means comprises an X-ray source and an X-ray detecting means, both being arranged so that a radiation path between them may cross said suspension at a predetermined position once a revolution.

* * * * *